United States Patent
Busche et al.

(10) Patent No.: US 7,922,893 B2
(45) Date of Patent: Apr. 12, 2011

(54) SYSTEM AND METHOD FOR PREPARING NEAR-SURFACE HEAVY OIL FOR EXTRACTION USING MICROBIAL DEGRADATION

(75) Inventors: Frederick D. Busche, Highland Village, TX (US); John B. Rollins, Southlake, TX (US); Harold J. Noyes, Golden, CO (US); James G. Bush, West Richland, WA (US)

(73) Assignee: International Business Machines Corporation, Armonk, NY (US)

( * ) Notice: Subject to any disclaimer, the term of this patent is extended or adjusted under 35 U.S.C. 154(b) by 1386 days.

(21) Appl. No.: 11/350,206

(22) Filed: Feb. 8, 2006

(65) Prior Publication Data

US 2007/0181300 A1  Aug. 9, 2007

(51) Int. Cl.
*B01J 29/70* (2006.01)
*C12Q 1/68* (2006.01)

(52) U.S. Cl. .............................................. 208/46; 435/6

(58) Field of Classification Search ........................ None
See application file for complete search history.

(56) References Cited

U.S. PATENT DOCUMENTS

| | | | |
|---|---|---|---|
| 4,522,261 | A | 6/1985 | McInerney et al. |
| 4,610,302 | A | 9/1986 | Clark |
| 4,799,545 | A | 1/1989 | Silver et al. |
| 4,905,761 | A | 3/1990 | Bryant |
| 4,971,151 | A | 11/1990 | Sheehy |
| 5,044,435 | A | 9/1991 | Sperl et al. |
| 5,163,510 | A | 11/1992 | Sunde |
| 5,339,254 | A * | 8/1994 | Matlock et al. ................. 702/19 |
| 6,649,400 | B2 * | 11/2003 | Fujita .......................... 435/252.4 |
| 6,758,270 | B1 | 7/2004 | Sunde et al. |
| 7,454,322 | B2 * | 11/2008 | Carpentier et al. ............. 703/10 |

OTHER PUBLICATIONS

Mishra et al. Evaluation of inoculum addition to simulate in situ bioremediation of oily-sludge-contaminated soil. Applied and Environmental Microbiology, 2001, vol. 67, p. 1675-1681.*
Coppinger, R., "In the pipeline?" The Engineer, Aug. 11, 2003.
Baldwin, J., "Up from the ground came a bubblin' crude," Nevada Daily Mail, Sep. 16, 2003.
Port, O., "Tapping Gushers Beneath the Gushers," Business Week Magazine, Jul. 11, 2005.
Goerold, W.T., "Sources of United States Oil Supply," Apr. 8, 2002, pp. 1-23.

* cited by examiner

*Primary Examiner* — Marjorie Moran
*Assistant Examiner* — Russell S Negin
(74) *Attorney, Agent, or Firm* — Andrea Bauer; Hoffman Warnick LLC

(57) ABSTRACT

A system and method for enhancing the recovery of heavy oil in an oil extraction environment by feeding nutrients to a preferred microbial species (bacteria and/or fungi). A method is described that includes the steps of: sampling and identifying microbial species that reside in the oil extraction environment; collecting fluid property data from the oil extraction environment; collecting nutrient data from the oil extraction environment; identifying a preferred microbial species from the oil extraction environment that can transform the heavy oil into a lighter oil; identifying a nutrient from the oil extraction environment that promotes a proliferation of the preferred microbial species; and introducing the nutrient into the oil extraction environment.

7 Claims, 2 Drawing Sheets

SYSTEM AND METHOD FOR PREPARING NEAR-SURFACE HEAVY OIL FOR EXTRACTION USING MICROBIAL DEGRADATION

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy. The Government has certain rights in the invention.

FIELD OF THE INVENTION

The invention relates generally to microbial degradation, and more specifically relates to a system and method for preparing near-surface heavy oil for extraction using microbial degradation, as well as an analytical infrastructure to support the extraction process.

BACKGROUND OF THE INVENTION

Heavy oil and bitumen deposits are found in many areas of the world, including Alaska, Canada, Siberia and the Nordic countries. Typically, deposits of heavy oil are mixed with deposits of lighter oil. Enhanced recovery of the heavy oil deposits generally require a reduction in viscosity, which refers to the propensity of a fluid to flow. Thus, in order to recover heavy oil, it must first be processed in some manner to reduce its viscosity to allow the oil to flow.

Currently, viscosity reduction is often accomplished either by: (1) increasing oil temperature through (a) injecting steam with or without gaseous additives such as methane, propane, natural gas, nitrogen, or $CO_2$, or (b) in-situ combustion through injecting oxygen-containing gases such as air; or (2) dilution of the oil through injecting low-viscosity hydrocarbon solvents. Enhanced oil recovery (EOR) on the North Slope of Alaska and similar locations is usually done with the use of heated steam injection. Heavy oils have such high viscosity at reservoir conditions that recovery rates by typical EOR methods are much lower than for lighter oils. Thus, the recovery of heavy oils has marginal economics or is uneconomical altogether. Challenges exist with EOR methods even when the oil reaches the well bore and production facilities because of asphaltic precipitation and the formation of emulsions. Although current technology is improving, the recovery of heavy oil remains costly to the point that many deposits are not economic to produce.

Today, long-reach, multilateral drilling techniques developed during the last 10 years are improving the economics of heavy oil production in areas such as the North Slope. At present, four percent of the oil in the trans-Alaska oil pipeline, some 35,000 barrels per day, is now heavy oil. This heavy oil is recovered using primarily $CO_2$ injection and gravity flow from horizontal production wells at formation depths of up to several thousand feet where formation temperatures range from around 70 degrees Fahrenheit to less than 100 degrees Fahrenheit. The heavy oil resource just on the North Slope is huge: the 20-25 billion barrels of heavy oil in place is more than was present at Prudhoe Bay before production started. While North Slope natural gas is the undeveloped resource that gets most of the attention from producers, there is actually more resource in heavy oil than there is in gas in Prudhoe, Point Thomson, and all the other gas discoveries on the North Slope in the greater Prudhoe Bay area.

Since $CO_2$ commonly occurs with natural gas, including as a component of natural gas, frequently there is an inexpensive way of obtaining the $CO_2$ that is needed to mobilize the oil. However, in many areas this supply is dwindling and now requires the piping of $CO_2$ from outside many of the fields to be used as a mobilizer for the oil. The production of steam to be used to mobilize the oil is also somewhat inefficient because of the energy that is necessary to create the heat to heat the water to produce steam is generally a poor substitute for $CO_2$. Since both processes have an inherent dependence upon the pathway through the formation to get to the heavy oil to be transported, there is a great deal of difficulty in focusing the solutions on the heavy oil to be transported. The heavy oil will either block the pore spaces or, as a result of some of the heavy oil being mobilized, create a channeling effect in the formation. In addition, with pressure buildup when forcing either $CO_2$ or steam into the formation containing the oil there is a great deal of potential that the formation will be fractured and thereby communication from the injection and recovery wells could be lost.

Accordingly, there is a need to alleviate the complications associated with tertiary recovery methods of heavy oil using $CO_2$ and steam.

SUMMARY OF THE INVENTION

The present invention addresses the above-mentioned problems, as well as others, by providing a system and method for preparing near-surface heavy oil for extraction using microbial degradation, as well as an analytical infrastructure to support the extraction process. As noted, heavy oil has both light and heavy fractions, and the present invention selectively enhances microbes (bacteria and/or fungi) that will metabolize only the heavy ends of the oil spectrum.

In a first aspect, the invention provides a method for enhancing the recovery of heavy oil in an oil extraction environment, comprising: sampling and identifying microbial species that reside in the oil extraction environment; collecting oil property data from the oil extraction environment; collecting nutrient data from the oil extraction environment; identifying a preferred microbial species from the oil extraction environment that can transform the heavy oil into a lighter oil; identifying a nutrient from the oil extraction environment that promotes a proliferation of the preferred microbial species; and introducing the nutrient into the oil extraction environment.

In a second aspect, the invention provides an analytical processing system for enhancing the recovery of heavy oil in an oil extraction environment, comprising: a data collection engine configured for receiving data relating to the oil extraction environment, wherein the data includes microbial species data, oil properties data and nutrient information that are identified as being germane to the oil extraction environment; a data warehouse for storing data collected from the data collection engine; and a data modeling system for analyzing data stored in the data warehouse and facilitating an identity of a preferred microbial species from the oil extraction environment that can transform the heavy oil into a lighter oil.

In a third aspect, the invention provides a computer program product stored on a computer usable medium for enhancing the recovery of heavy oil in an oil extraction environment, comprising: program code configured for receiving data relating to the oil extraction environment, wherein the data includes microbial species data, oil properties data and nutrient information that are identified as being germane to the oil extraction environment; program code configured for storing the received data in a data warehouse; and program code configured for analyzing data stored in the data warehouse and facilitating an identity of a preferred microbial species from the oil extraction environment that can transform the heavy oil into a lighter oil.

In a fourth aspect, the invention provides a method for implementing an application for enhancing the recovery of heavy oil in an oil extraction environment, comprising: providing a computer infrastructure being operable to: receive data relating to the oil extraction environment, wherein the data includes microbial species data, oil properties data and nutrient information that are identified as being germane to the oil extraction environment; store the received data in a data warehouse; and analyze data stored in the data warehouse to facilitate an identity of a preferred microbial species from the oil extraction environment that can transform the heavy oil into a lighter oil.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Microbial Degradation Overview

Figure 1:
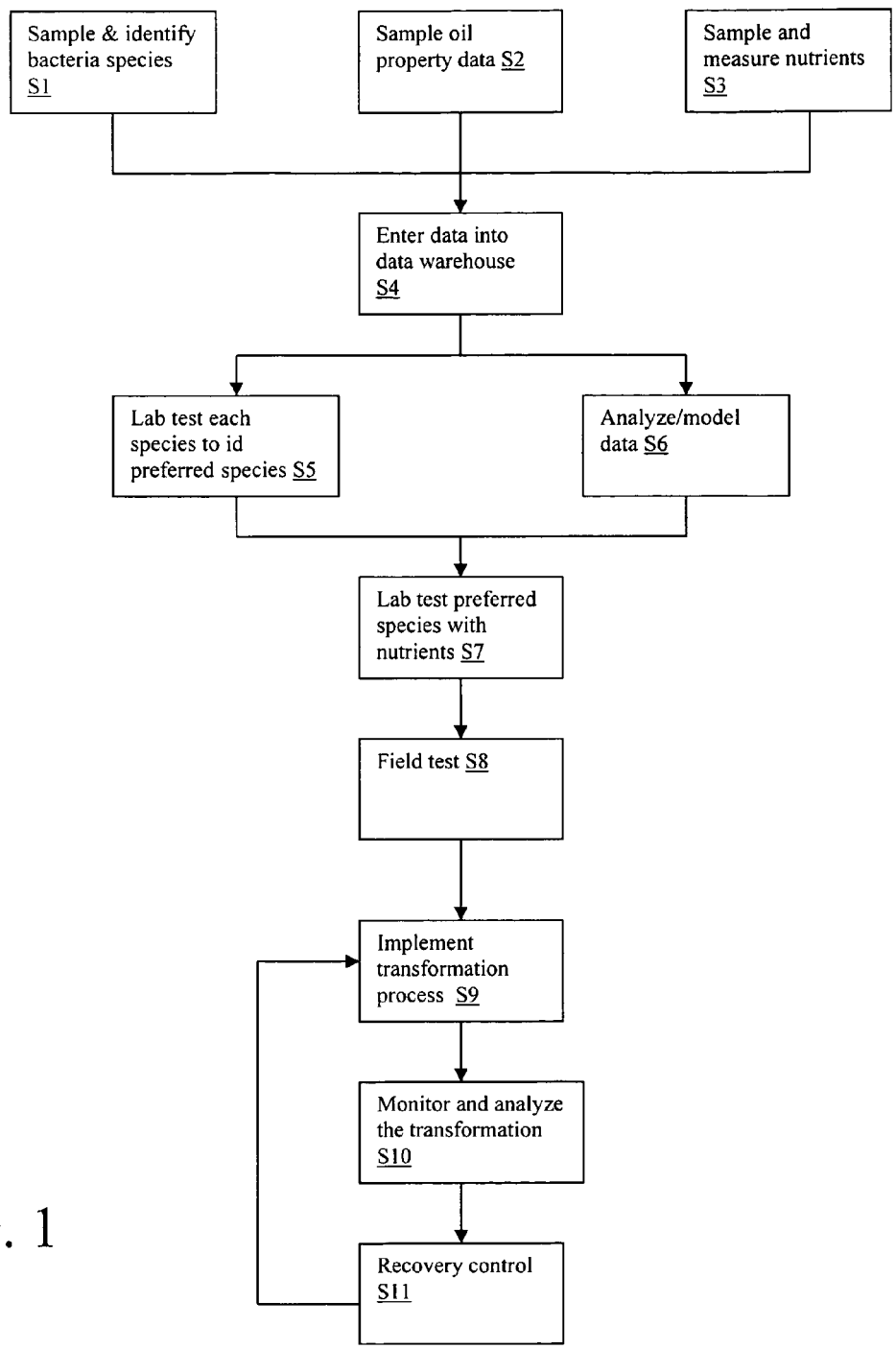
FIG. 1 depicts a flow diagram depicting a method of obtaining heavy oil in accordance with the present invention.

Given that the heavy oil on the North Slope and other places around the Arctic Circle is located in a near-surface environment similar to that associated with near-surface petroleum product spills, the present invention proposes the use of a process similar to the ones used to clean up those spills (referred to as biological remediation or simply bioremediation) to enhance the recovery of heavy oil.

Biological remediation is the process of using microbes or microorganisms to clean up and detoxify a subsurface environment that contains toxic chemicals such as petroleum as well as crude oil. These microbes are typically bacteria from the phyla such as Actinobacteria, Aquificae, Bacteroidetes/ChlorobiChlamydiae/Verrucomicrobia, Chloroflexi, Chrysiogenetes, Cyanobacteria, Deferribacteres, Deinococcus-Thermus, Dictyoglomi, Fibrobacteres/Acidobacteria, Firmicutes, Fusobacteria, Gemmatimonadetes, Nitrospirae, Omnibacteria, Planctomycetes, Proteobacteria, Spirochaetes, Thermodesulfobacteria, Thermomicrobia, and Thermotogae. Such bacteria are able to thrive in such an environment and synthesize harmful substances into energy.

Biochemical reactions, or pathways, in an organism that result in activity, growth, and reproduction are what drive the remediation. These processes include degradation (catabolic) and biosynthetic (anabolic) processes. Catabolic processes break down larger molecules into simpler components, producing energy for microbial growth and reproduction. Organic contaminants can be transformed into less harmful forms or degraded completely (mineralized) to inorganic components through these catabolic processes.

Some of the most important factors that control the metabolic process include: (1) the chemicals in the environment that serve as nutrient and energy sources; (2) enzymes, which are catalysts to the metabolic reactions that occur in the cell; and (3) oxidation-reduction reactions, which allow release and biological conservation of energy. Metals can serve important roles as electron donors or electron acceptors in these reactions.

Carbon, nitrogen, and phosphorus are the basic elemental components of the most common molecules in a cell (proteins, sugars, and nucleic acids). Organisms that require an organic or complex source of carbon are called heterotrophs. Those that use inorganic sources of carbon like carbon dioxide ($CO_2$) are called autotrophs. Most microorganisms need nitrogen because it is a major constituent of proteins and nucleic acids. Nitrogen can be found in nature in both organic and inorganic forms. However, the most abundant forms of nitrogen in nature are inorganic—either ammonia ($NH_3$), nitrate ($NO_3^-$), or nitrogen gas ($N_2$). Most microbes can use either ammonia or nitrate as their sole nitrogen source. All of these potential nutrients occur naturally within the North Slope formations. The methodology of stimulating the growth of in-situ bacteria has been used with particular success with petroleum product and crude oil spills into soils and formations that are in the near surface environment.

Transformation Process

The heavy oil recovery process that is described herein involves the utilization of in-situ microbial species (e.g., bacteria or fungi) in near-surface heavy oil containing formations (such as the North Slope) in order to reduce the viscosity of the heavy oil. The process involves the feeding of a microbial species that is specific to the heavy fractions in the oil in order to convert heavy oil into lighter oil. Although the invention could be practiced in any heavy oil environment, the process is particularly applicable to deposits having low pressure and near surface temperatures, such as those found in the North Slope deposits. These conditions, which allow for the growth of species, are rather uncommon in deeper oil reservoirs because of their higher pressures and temperatures.

An illustrative flow diagram for implementing the process is shown in FIG. 1. The process begins at steps S1, S2 and S3 with the collection and sampling of data germane to a specific heavy oil producing formation (i.e., environment). Namely, at step S1, data is collected and sampled relating to the identification of the microbial species that naturally occur within the various interstices or pore spaces in the producing formation of interest. In addition, at step S2, data is collected and sampled relating to the chemistry, molecular structure, and physical properties of the rock and fluid system to provide an assessment of the controls on viscosity, such as pH levels, redox conditions, clay components, mineralogy, etc. Also, at step S3, the nutrient availability within these formations is sampled and measured. Analysis of core samples may be utilized to obtain some of the aforementioned data including microscopic as well as chemical and physical property measurements.

In order to assess the species diversity (step S1) and the nutrient availability (step S3), extreme care should be taken in collecting formation samples. The samples must be preserved such that their in-situ environment is not disturbed paying particular attention to the preservation of the reservoir temperature and pressure of the sample as well as its oxidation-reduction state, organic species diversity and gaseous components. Once the samples have been returned to the laboratory, each microbial species must be identified as well as the pertinent information about the in-situ environment.

At step S4, data captured from the samples is entered into a data warehouse. The resulting data warehouse will thus provide a data repository of the biological, physical, chemical and geological information associated with the formation.

That data is then analyzed and modeled at step S6 to facilitate: (1) the identification of a set of microbial species from all of the identified species, which are capable of transforming heavy oil into lighter oil within a specific range of reservoir conditions, i.e., a set of "degradation species," and (2) the type and amount of nutrients required to feed the identified species to achieve the desired type and rate of transformation such that fluid flow is not impaired by an overabundance of microbiological organisms.

Along with the data analysis and modeling, the microbial species samples must be tested in a simulated reservoir environment at step S5 to identify those species that preferentially feed upon the heavy fractions of the oil within those interstices found in the heavy oil environment. Ultimately, based on the data analysis and lab testing, one (or more) preferred microbial species is identified that can most effectively convert heavy oil into lighter oil. Next, at step S7, lab testing of the preferred species must be performed to understand their acceptance of supplemental nutrition that may be provided to them. This testing will allow for an assessment of the amount of additional nutrients that must be added to the formation to allow for the preferential growth of the preferred microbial species that would preferentially degrade the heavy oil fractions. The information collected and analyzed in steps S5, S6, and S7 can be fed back into the data warehouse to allow for continued analysis and modeling.

Because of the many variables that exist as a result of this characterization, it may be necessary to use statistical as well as discovery-based analysis (such as associations, sequential patterns, and clustering analysis) to adequately understand the data produced, using a tool such as IBM's INTELLIGENT MINER™ (IM). Again, before hypotheses have been formulated, analysis of the data at step S6 using such predictive algorithms as "transform regression" analysis must be conducted on the data for a thorough understanding of what would be predicted to take place and what attributes would be necessary to define success.

Once the data has been analyzed and a successful identification of a preferred species and required nutrients has occurred, then field testing is implemented at step S8 in order to pilot the frequency of nutrient supply, rest states necessary for the reactions to take place, and production efficiencies that are realized. Once the complete process has been defined, then scale-up to production occurs and the transformation process is implemented at step S9, in which the introduction of supplemental nutrients into the environment should cause the identified species to propagate and transform the heavy oil into lighter oil. The introduction of nutrients may be done in existing wells.

At step S10, the in-situ environment is monitored such that transformation data is collected and is stored in the data warehouse. The transformation data is then analyzed and modeled at step S10 in order to, among other things, track the transformation and predict future behavior. If a correction is required, a recovery control process can be implemented to address the issue at step S11. The recovery control process may include a reduction in or cessation of feeding.

The advantages of this approach over current methods to reduce oil viscosity are:
1. The process can utilize existing wells.
2. The process should reduce or eliminate the usage of $CO_2$ or steam injection.
3. There will be a reduction in the risk associated with undesired formation fracturing and surface and subsurface environmental disturbance.
4. Because nutrients will be delivered using a pulsing technique (delivery a slug of nutrients followed by a rest period to allow the bacteria to process the nutrients), there may be a reduced need for continuous operation and therefore a cost savings associated with the oil recovery.
5. Stimulation of bacteria with nutrients may have the additional benefit that the bacteria will produce surfactants that will enhance the flow of the oil.
6. The process will reduce the gravity (or increase the API gravity) of the oil in place, thus enabling the oil to flow better through the formation.
7. As a result of the analysis of the data before the process begins, modeling of results can be done to lessen the possibility of failure and predict the conditions that will contribute to optimization of oil production.

Figure 2:
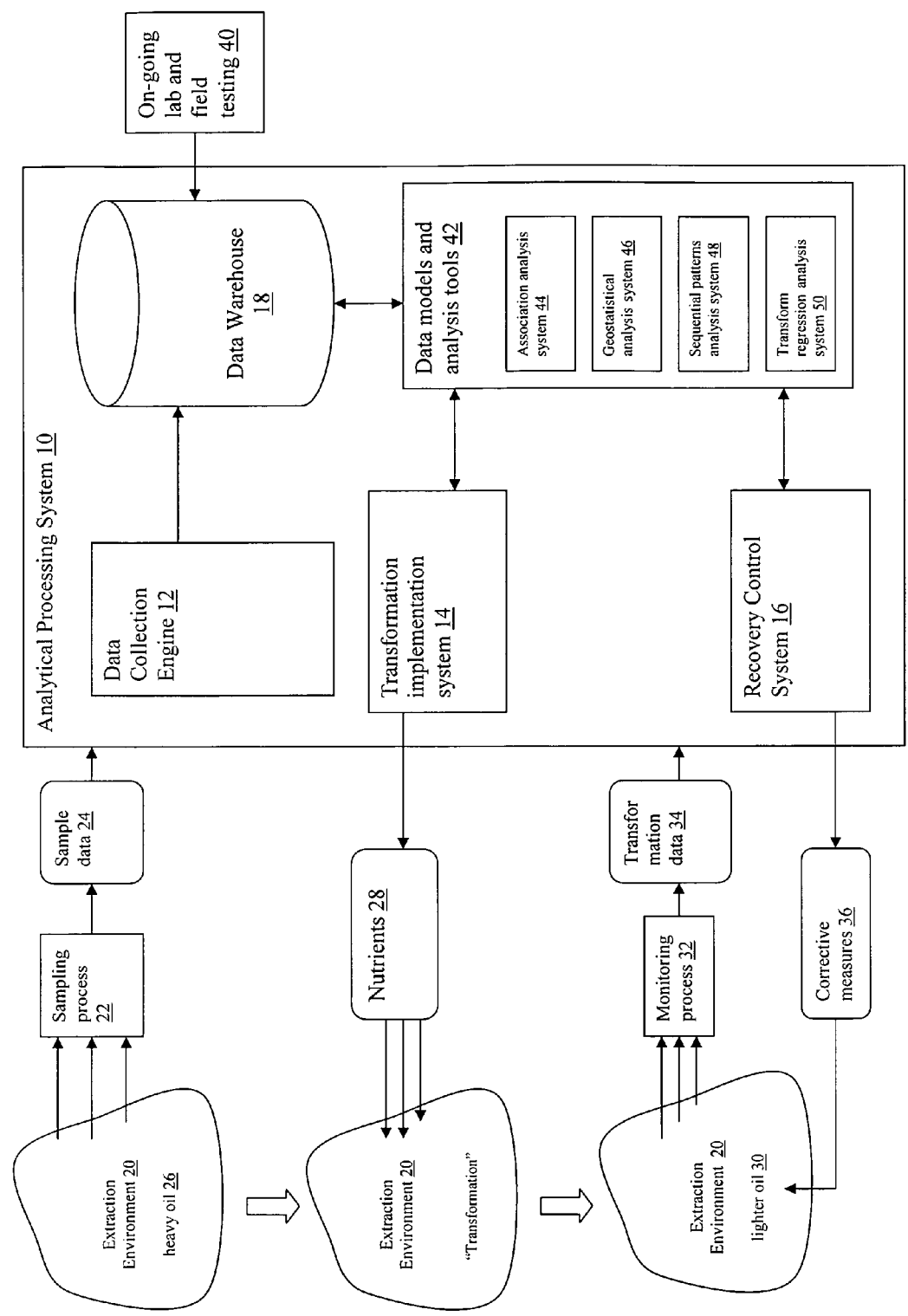
FIG. 2 depicts an analytical processing system for implementing a heavy oil recovery process in accordance with the present invention.

Referring now to FIG. 2, an analytical processing system 10 is shown for managing a transformation process, such as that described above in FIG. 1. On the left hand side of the diagram an oil extraction environment 20 is shown in three stages in which a heavy oil component 26 is transformed into a lighter oil component 30. In the first stage, a sampling process 22 at the oil extraction environment 20 is used to collect a set of sample data 24, which is imported into the analytical processing system 10 via a data collection engine 12. Once imported, the data is stored in a data warehouse 18. Additional data resulting from, e.g., ongoing lab and field testing 40, data previously obtained from drilling in the environment 20, data previously gathered regarding microbial species, nutrients, geological data, etc., may also be imported into the data warehouse 18.

As noted above, the ultimate goal of the process is to identify nutrients 28 that can be introduced into the oil extraction environment 20 to feed a preferred microbial species to result in a transformation by causing the preferred species to propagate and degrade the heavy oil 26 into lighter oil 30. In the second stage, transformation implementation system 14 is utilized to model the environment in order to identify a preferred species, select nutrients 28 to enhance growth of the preferred species, and predict the resulting impact on the oil extraction environment 20. In order to achieve this, various data models and analysis tools 42 may be utilized.

Examples of these data models and analysis tools 42 may for example include: (1) an association analysis system 44 to, e.g., track how the subsurface environment varies from well to well in the extraction environment 20 with regard to associated attributes both geologic and biologic; (2) a geostatistical analysis system 46 to estimate the conditions between bore holes to ascertain the rate of change of conditions and therefore the possible speciation change that might occur from well to well across the field as well as changes in flow well communication that might be present in the field; (3) a sequential patterns analysis system 48 that provides for analysis and prediction, and in which operation protocols can be modified automatically to control changes that are or may occur across the environment during operation; and (4) a transform regression analysis system 50. In one illustrative embodiment, a data model may be derived from mining operations involving production and exploration data models.

In the third stage, once the transformation has taken place, and the heavy oil gets converted to lighter oil 30, a monitoring process 32 is utilized to generate transformation data 34, which is likewise imported into the analytical processing system 10 via the data collection engine 12, and stored in data warehouse 18. Transformation data 34 may include any information related to conditions (e.g., microbiological changes, pH levels, etc.) and production (e.g., flow rates). Transformation data 34 may also be collected in any manner, e.g., electrical monitoring devices, etc. The transformation data 34 is also continuously analyzed by the data models and analysis tools 42 to ensure that the transformation process is behaving as predicted. Predictive modeling may be implemented to predict any negative outcomes before they occur. Based on the results of these models, corrective measures 36 may be introduced back into the oil extraction environment 20 by recovery control system 16 to address current problems or head off any predicted problems (e.g., adjusting the amount or type of nutrients). This process allows for the understanding of progress both negatively and positively across the heavy oil accumulation to be monitored such that control of results can be semi-controlled. The introduction of corrective measures 36 may first be investigated under laboratory conditions such that a predictive model could be produced and then applied to the geostatistical assessment of the underlying geology to predict what changes might take place.

In general, analytical processing system 10 may comprise any type of computing environment, and could be implemented as part of a client and/or server. Analytical processing system 10 may utilize one or more computers that generally include processors, input/output (I/O) devices, and memory. Processing capabilities may be implemented in a single processing unit, or be distributed across one or more processing units in one or more locations, e.g., on a client and server. Memory may comprise any known type of data storage and/or transmission media, including magnetic media, optical media, random-access memory (RAM), read-only memory (ROM), a data cache, a data object, etc. Moreover, data warehouse 18 may reside at a single physical location, comprising one or more types of data storage, or be distributed across a plurality of physical systems in various forms.

I/O devices may comprise any system for exchanging information to/from an external resource. External devices/resources may comprise any known type of external device, including a monitor/display, speakers, storage, another computer system, a hand-held device, keyboard, mouse, voice recognition system, speech output system, printer, facsimile, pager, etc. Although not shown, additional components, such as cache memory, communication systems, system software, etc., may be incorporated into analytical processing system 10.

Access to analytical processing system 10 may be provided over a network such as the Internet, a local area network (LAN), a wide area network (WAN), a virtual private network (VPN), etc. Communication could occur via a direct hard-wired connection (e.g., serial port), or via an addressable connection that may utilize any combination of wireline and/or wireless transmission methods. Moreover, conventional network connectivity, such as Token Ring, Ethernet, WiFi or other conventional communications standards could be used. Still yet, connectivity could be provided by conventional TCP/IP sockets-based protocol. In this instance, an Internet service provider could be used to establish interconnectivity. Further, as indicated above, communication could occur in a client-server or server-server environment.

It should be appreciated that the teachings of the present invention could be offered as a business method on a subscription or fee basis. For example, an analytical processing system 10 comprising a data warehouse 18, transformation analysis system 14, and/or recovery control system 16 could be created, maintained and/or deployed by a service provider that offers the functions described herein for customers. That is, a service provider could offer to provide a data processing system for supporting near-surface heavy oil extraction using microbial degradation as described above.

It is understood that the systems, functions, mechanisms, methods, engines and modules described herein can be implemented in hardware, software, or a combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. In a further embodiment, part or all of the invention could be implemented in a distributed manner, e.g., over a network such as the Internet.

The present invention can also be embedded in a computer program product, which comprises all the features enabling the implementation of the methods and functions described herein, and which—when loaded in a computer system—is able to carry out these methods and functions. Terms such as computer program, software program, program, program product, software, etc., in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. A method for enhancing the recovery of heavy oil in an underground, near-surface crude oil extraction environment, comprising:
    sampling and identifying microbial species (bacteria and/or fungi) that reside in the underground, near-surface crude oil extraction environment;
    collecting rock and fluid property data from the underground, near-surface crude oil extraction environment;
    collecting nutrient data from the underground, near-surface crude oil extraction environment;
    identifying a preferred microbial species from the underground, near-surface crude oil extraction environment that can transform the heavy oil into a lighter oil;
    identifying a nutrient from the underground, near-surface crude oil extraction environment that promotes a proliferation of the preferred microbial species; and
    introducing the nutrient into the underground, near-surface crude oil extraction environment.

2. The method of claim 1, wherein the step of identifying a preferred microbial species includes the steps of:
    entering nutrient data, oil property data and data relating to the microbial species residing in the underground, near-surface crude oil extraction environment into a data warehouse;
    modeling the data in the data warehouse to facilitate the identification of a preferred microbial species.

3. The method of claim 2, wherein the step of identifying a preferred microbial species further includes performing lab tests.

4. The method of claim 1, comprising the further steps of:
    monitoring the underground, near-surface crude oil extraction environment and collecting transformation data; and taking a corrective action based on an analysis of the transformation data.

5. The method of claim 4, comprising the further steps of: storing the transformation data in a data warehouse; and modeling the transformation data to predict an outcome.

6. The method of claim 5, wherein the modeling steps include performing an analysis selected from the group consisting of: an association analysis, a geostatistical analysis, a sequential pattern analysis, and a transform regression analysis.

7. The method of claim 1, wherein the preferred microbial species is selected from the group consisting of bacteria and fungi.

* * * * *